(12) United States Patent
Parrell et al.

(10) Patent No.: US 8,943,681 B2
(45) Date of Patent: Feb. 3, 2015

(54) DEVICE FOR INTERNAL FLAW MAGNIFICATION DURING WIRE DRAWING

(75) Inventors: Jeff Parrell, Roselle Park, NJ (US); Boleslaw Czabai, Avenel, NJ (US); Youzhu Zhang, East Brunswick, NJ (US); Seungok Hong, New Providence, NJ (US); Michael Field, Jersey City, NJ (US)

(73) Assignee: Oxford Superconducting Technology, Carteret, NJ (US)

( * ) Notice: Subject to any disclaimer, the term of this patent is extended or adjusted under 35 U.S.C. 154(b) by 963 days.

(21) Appl. No.: 12/451,589

(22) PCT Filed: May 21, 2007

(86) PCT No.: PCT/US2007/012063
§ 371 (c)(1),
(2), (4) Date: Dec. 28, 2009

(87) PCT Pub. No.: WO2008/143615
PCT Pub. Date: Nov. 27, 2008

(65) Prior Publication Data
US 2010/0101076 A1    Apr. 29, 2010

(51) Int. Cl.
*G01N 3/20* (2006.01)
*B23P 17/00* (2006.01)

(52) U.S. Cl.
CPC .......... *G01N 3/20* (2013.01); *G01N 2203/0062* (2013.01); *G01N 2203/028* (2013.01); *G01N 2203/0435* (2013.01)
USPC .................. 29/749; 29/755; 29/868; 73/600; 140/93 R

(58) Field of Classification Search
USPC .............. 29/749, 755, 868, 605, 599; 73/599, 73/600; 356/21; 140/93 R
See application file for complete search history.

(56) References Cited

U.S. PATENT DOCUMENTS

| | | | |
|---|---|---|---|
| 2,280,500 A | 4/1942 | Reybum | |
| 3,471,925 A | 10/1969 | Bindari | |
| 4,178,676 A * | 12/1979 | Dustmann et al. | 29/599 |
| 4,380,931 A * | 4/1983 | Frost et al. | 73/599 X |
| 4,808,926 A | 2/1989 | Graham et al. | |
| 5,673,475 A * | 10/1997 | Takahashi | 29/755 |
| 6,301,944 B1 | 10/2001 | Offer | |
| 6,526,077 B1 * | 2/2003 | Tabirian | 356/21 X |
| 6,694,584 B1 | 2/2004 | Ahrens | |

FOREIGN PATENT DOCUMENTS

JP           01110800 A  *  4/1989 ...................... 29/749

* cited by examiner

Primary Examiner — A. Dexter Tugbang
(74) Attorney, Agent, or Firm — Klauber & Jackson LLC

(57) ABSTRACT

A device for use as an adjunct in assuring that a manufactured wire is substantially free of internal flaws. A plurality of successively adjacent wire bending stations are provided, where each station includes means for bending the wire into bending planes which are different for each of the stations. The wire is passed through the successive stations, whereby the different bending planes at each station subject the wire at each station to tensile bending strain at portions of the wire cross-section which are different for each station. As a result the probability is increased that a given internal flaw in the wire will be exposed to the tensile bending strain condition as the wire passes through the successive stations, increasing likelihood of breakage of the wire at the flaw or of flaw magnification to improve detection of the flaw during subsequent wire inspections.

13 Claims, 2 Drawing Sheets

DEVICE FOR INTERNAL FLAW MAGNIFICATION DURING WIRE DRAWING

The present application is a national stage application claiming the priority of copending PCT Application No. PCT/US2007/012063, filed May 21, 2007, and Applicants claim the benefits of 35 U.S.C. §120 as to the PCT application, the entire disclosure of which is incorporated herein by reference.

FIELD OF INVENTION

This invention relates generally to wire manufacture and processing, and more specifically relates to apparatus and methodology useful in assuring that a manufactured wire is substantially free of internal flaws.

BACKGROUND OF THE INVENTION

Wire drawing is the method used to produce most wire products. By way of example, consider the fabrication process of multifilamentary composite superconducting wire—a technology of particular interest for the present invention. One common wire type used for superconducting electromagnets consists of Nb-47 wt % Ti filaments within a Cu matrix. As is known in the prior art, such composite wires are commonly produced by stacking an assemblage of Nb—Ti alloy rods into a copper tube or can, extruding the assemblage to rod, and drawing the rod into the wire used for magnet winding. Small defects or flaws can occasionally occur internally in the resulting wire, caused for example by foreign material particles inadvertently incorporated into the composite during billet assembly, or flaws formed during drawing due to inadequate bonding at interior surface interfaces, such as where the Nb—Ti rods interface with the copper matrix.

Although undesirable, flaws are a nearly unavoidable practical occurrence in the large-scale production of wire. This reality is in conflict with the requirement that a wire must be absolutely free of flaws to be functional in persistent-current superconducting magnets, for applications such as Magnetic Resonance Imaging (MRI). Thus, it is a critical quality assurance step for the manufacturing of superconducting wire that flaws are detected and removed from the final wire before it is used in a magnet.

A prior art technique for finding flaws, eddy current testing, is commonly used in wire manufacturing for flaw detection. However, given the heavily surface biased phenomenon nature of the eddy current signal, and the fact that the superconducting filaments in a wire are typically far from the wire surface, eddy current testing alone is often inadequate for detecting the presence of filament breaks in the wire interior. Thus, additional means of detecting or eliminating such flaws in the internal wire structure are desirable.

According to the theory of bending, as described by Dieter (*Mechanical Metallurgy*, G. E. Dieter, McGraw-Hill, Inc., 1986), the bending strain of a specific 'fiber' at a given location within the wire varies across the wire diameter. At the middle of the wire thickness is a neutral axis at which the strain on a wire fiber is zero. The strain at other locations within the wire thickness is proportional to the distance from this neutral axis, with the fibers on the outer wire surface being strained in tension, and the fibers on the inner surface being compressed. For the purposes of bending a wire so as to open (break) its flaws, it is the tensile strain that is important; compressive strains at a flaw (e.g. a crack) will not serve to open or magnify the flaw. This aspect of bending is germane to the present invention, i.e. the fact that the only wire section placed into tension is the outer surface of the wire in contact with the roller. The cumulative result of these actions is that it turns an internal flaw into a surface component, more easily detected by conventional eddy current testing and high-speed laser micrometer measurement.

Wire straighteners, also known as cast-killing rolls, have originally been commercially produced to remove or "kill" the cast of a wire. In this method, a set of small diameter rollers is placed within the wire movement path. The typical wire straightener roll set consists of three rollers arranged at the vertices of a triangle. The diameter of the rollers is small enough to cause the wire to experience significant bending strain as the rollers bend the wire. Traditionally this strain is used to remove cast from a wire. Although these wire straighteners could be used to gain some of the benefit of the present invention, prior art straightening rolls are not optimized for the purposes of the present invention.

While it is thus possible to use prior art straightening rolls to expose internal flaws of a multifilamentary wire, the drawbacks are as follows:

1) In prior art roller arrangements, the wire is in contact with the rollers over just a few degrees of the roller circumference, resulting in little penetration of bending strain into wire 2) Typical straightening rolls setups are in one plane, sometimes multiple planes, but never have the forward and reverse bends in each plane of operation. This is a critical improvement in the invention disclosed here.

3) By itself, wire straightening rolls may amplify a defect yet not break the wire, allowing a defect to pass into final product. It is more desirable for the bending process to actually break the wire, ensuring it is not allowed to pass into final product.

SUMMARY OF THE INVENTION

Now in accordance with the present invention, apparatus and methods are disclosed which result in the desired improved flaw detection and removal. Pursuant to the invention the wire is controllably bent in such a manner as to expose or magnify wire interior flaws, and the disclosed inspection process helps more easily detect the flaws magnified by the controlled bending.

In one aspect of the invention a device is disclosed for use as an adjunct in assuring that a manufactured wire is substantially free of internal flaws, In such device a plurality of successively adjacent wire bending stations are provided, where each station includes means for bending the wire into bending planes which are different for each of the stations. The wire is passed through the successive stations, whereby the different bending planes at each station subject the wire at each station to tensile bending strain at portions of the wire cross-section which are different for each station. As a result the probability is increased that a given internal flaw in the wire will be exposed to the tensile bending strain condition as the wire passes through the successive stations, increasing likelihood of breakage of the wire at the flaw or of flaw magnification to improve detection of the flaw during subsequent wire inspections.

The device consists of roller pairs positioned on at least three planes that intersect in a line coincident with the axis of wire drawing. The roller pairs on each of the three planes are sized so as to achieve a specific level of bending strain in the wire being drawn. The described three-plane serpentine roller device is an improvement over existing single plane cast killing or straightening rolls in that the use of roller pairs arranged on multiple planes with forward and reverse bends on each plane, and with each bend over 180° of bending roll, greatly increases the probability that a given internal wire structural flaw will be exposed to the maximum tensile bending strain condition as the wire passes through the device. The purpose of exposing a wire flaw to a tensile bending strain is to assist in detection and removal of such flaws from the wire product, either by breaking the wire at the site of the internal flaw for the case of larger sized flaws; or for smaller defects by increasing the size of the flaw, thereby enabling improved flaw detection by conventional means such as eddy current testing. The device is especially useful for the application of multifilamentary composite superconducting wire in superconducting magnets, an application where no flaws in the superconducting filaments of the wire can be tolerated, and yet these can be difficult or impossible to detect by eddy current testing alone. This limitation is overcome in the present invention by the use of multiple bending roller sets, each arranged on one of at least three different planes, all of which intersect at a line coincident with the wire path.

In a further aspect of the invention an improvement is provided in the method for manufacturing a superconducting magnet which includes winding the magnetic coil with a superconducting wire; and wherein the acceptability of the resulting magnet is determined by the capability of the magnet to carry a persistent electric. The improvement increases the likelihood of the magnet having the cited acceptability by utilizing for the winding only superconducting wire which has passed a quality inspection procedure which includes flaw detection by a method which incorporates bending of the wire into sufficiently different bending planes as to subject substantially all of the wire in each of its transverse cross-sections to tensile bending strain. This serves to magnify flaws which may be present in the wire and thereby increase the likelihood of detection of the flaws. By "bending plane" is meant the plane bordered by the bent wire.

BRIEF DESCRIPTION OF DRAWINGS

The invention is diagrammatically illustrated, by way of example, in the drawings appended hereto, in which.

DESCRIPTION OF PREFERRED EMBODIMENTS

Figure 1:
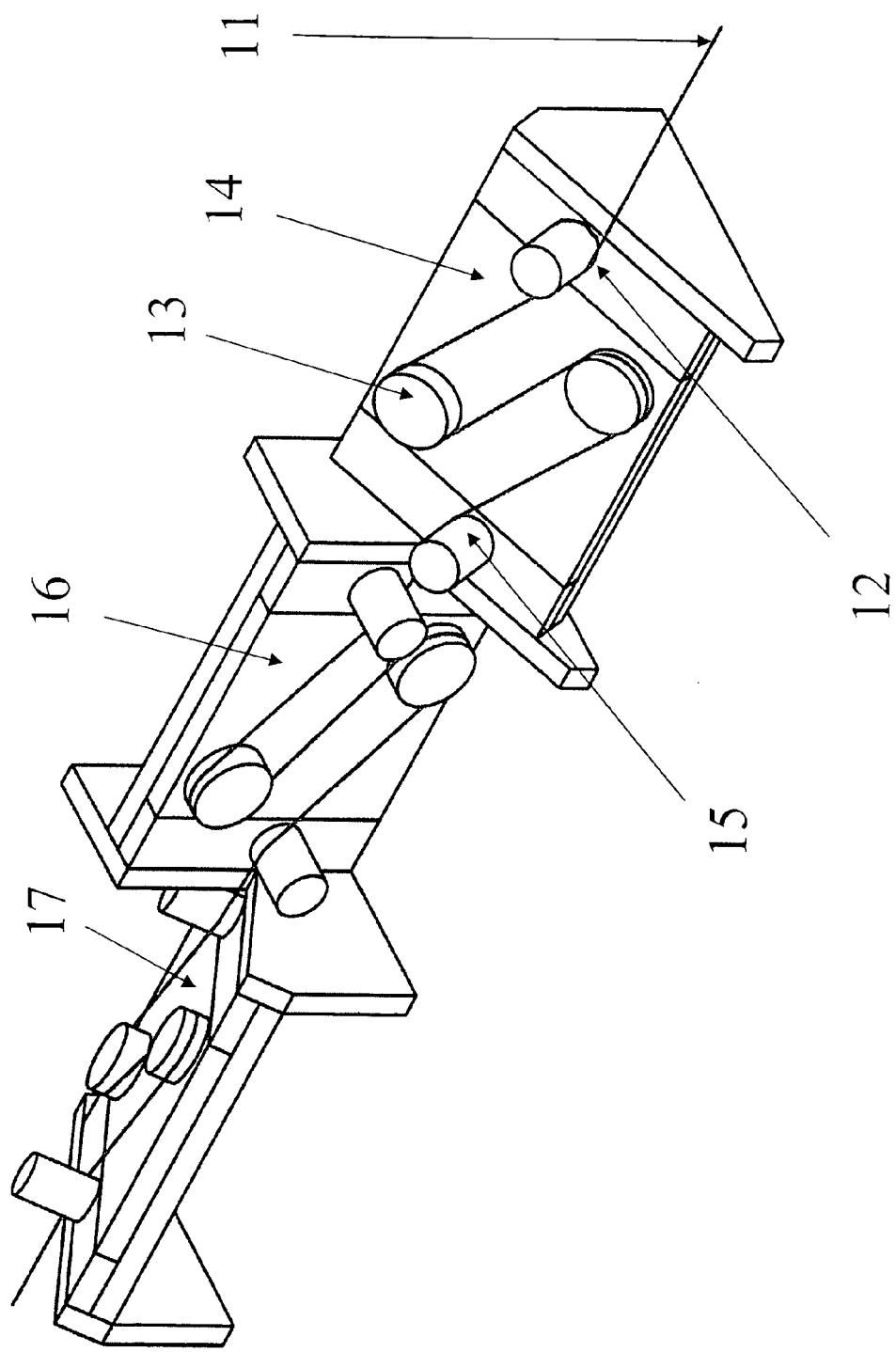
FIG. 1 is perspective view, schematic in nature, of a device or apparatus in accordance with the present invention, and shows the wire path through the apparatus.

A schematic perspective drawing of the apparatus aspects of the invention is shown in FIG. 1. The device depicted can be run in-line during wire drawing operations, so that extra manufacturing steps are not required. The wire 11 enters the device at point 12, and is wrapped around the bending rollers 13. As the wire passes from one planar roller set 14 to another, guide rollers 15 are used to keep the wire in position and from contacting the fixture frame.

Figure 2:
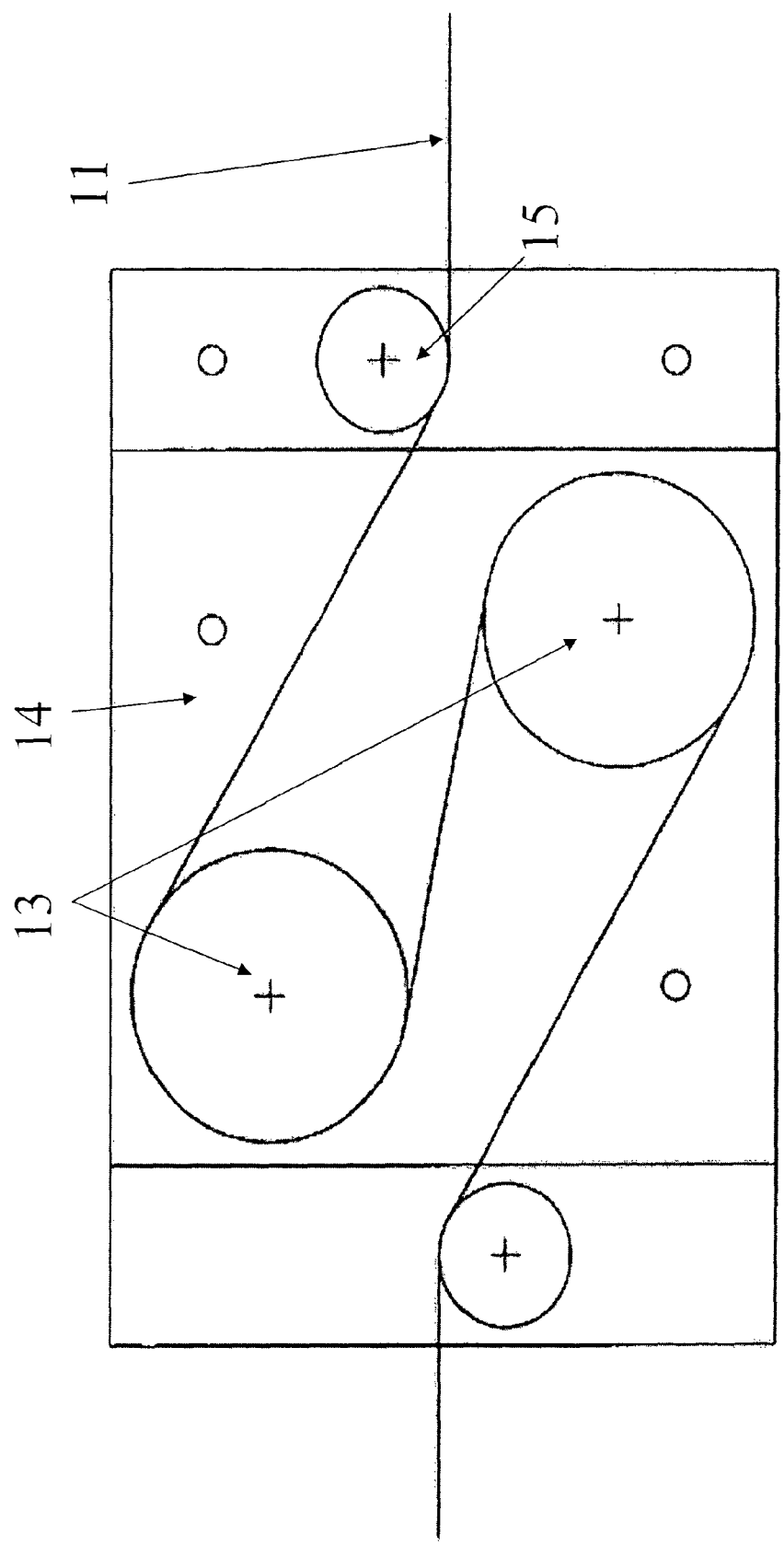
FIG. 2 is a schematic top plan view of one of the three bending stations present in the FIG. 1 apparatus, showing how this station bends the wire in opposite directions, on two opposing sides.

A single planar roller set 14 is shown in more detail in FIG. 2. The wire 11 makes contact with the two bending rollers 13 so as to achieve a state of tension in the wire surface on "two sides" of the wire; the surface of the wire placed into tension on one roller becomes the surface in compression when the wire passes through to the other roller in the planar set, and vice-versa. Thus, after passing through the first of these planar sets of rollers, two pie slice sections around the 360° circumference of the wire have been subjected to the maximum flaw-killing deformations. The planar roller sets 14 should be as close to each other as possible to minimize the chance of the wire shifting angular position relative to the 360° wire circumference as it moves from one plane of rollers to the other, i.e. twisting of the wire. Referring back to FIG. 1, after the wire leaves the first planar roller set 14, it encounters a second planar set 16 oriented at an angle around the wire circumference that is different from the first planar set. After leaving the second planar set of rollers, there are now four sections around the 360° circumference of the wire that have been subjected to the most effective flaw-killing deformations. After the wire leaves the second planar roller set, it enters the third roller set 17, which is oriented at an angle around the wire circumference that is different from either of the first two planar roller sets. After leaving this third set of rollers, there are now six sections around the wire circumference that have been subjected to the most effective flaw-killing stresses. This has been found experimentally to very effectively give complete coverage of the wire circumference, exposing all flaws inside the wire.

Although this specific example illustrates the use of two rollers per planar roller set, and three planar sets arranged at equal angles 120° apart, it will be apparent that additional rollers or planar rollers sets could be incorporated. However, with each additional roller and roller set the force required to pull the wire through the assembly increases, and to operate the device in-line during wire drawing requires that the pull force be minimized to reduce wire breakage simply due to excessive line tension. The use of three planar sets is a good compromise in this regard; it provides good coverage around the 360° wire circumference, and does not require excessive force to pull the wire through the rollers.

In addition to the location within the wire depth or thickness, the bending strain experienced by a given wire fiber also depends on the diameter of the roller in contact with the wire, with the strain increasing with decreasing radius of curvature. This means that in order to achieve a nominally constant bending strain over a range of wire sizes, various sizes of rollers 13 must be used. The roller diameter is selected experimentally so as to lead to wire breakage when flaws of a particular type are encountered, and yet not damage wire that is free of flaws before entering the assembly.

While in many cases the rollers will extract the flaw by wire breakage, the usage of standard eddy current testing and laser micrometer diameter measurement machines insures that internally damaged wire is detected and flaws extracted. An eddy current machine uses eddy currents induced by an alternating magnetic field to probe for discontinuities in the surface or near subsurface of a wire. A laser micrometer machine uses lasers to detect diameter changes, an indication of flawed wire. Both machines can be set up in a wire drawing path so that they can stop the line automatically when a flaw is detected. The line operator can then inspect the stopped wire to verify the signal and extract the flawed section of the wire.

In order to illustrate the efficacy of the invention, a device as described and illustrated in FIG. 1, using 1.8 mm diameter roller size, was used in processing a ~1.6 mm wire. A slight back tension was set on the line, so as not to unduly stretch the wire; the purpose is to keep the wire taut during the serpentine operation so the wire does not fall off the rollers. Some flaws are large enough to cause a wire break during the serpentine operation when being subjected to the forward or reverse bending strain in one of the three planes, of which a single example plane is shown in FIG. 2. Immediately after the serpentine operation, the wire is drawn through a finishing or final size wire die, and then through a tandem of an eddy current and laser micrometer machines for flaw detection. A Magnetic Analysis MAC 150 eddy current machine and a Beta Lasermike Holix 5007 HP laser micrometer were used for these purposes. These machines are used to detect sudden dimensional changes, a sign that an internal flaw that has "necked" the wire, i.e. locally reduced the wire diameter, which has been made significantly more prominent by the serpentine operation. Therefore the preferred embodiment is used both to cause wire breaks at large flaw points and magnify smaller flaws so that they may be picked up at subsequent conventional inspection steps. The preferred embodiment does not create a flaw where there was none previously; it just magnifies the existence of small flaws for purposes of removal. Table 1 illustrates the parameters for a number of sets.

TABLE 1

| Set# | Wire diameter | Roll diameter |
|------|---------------|---------------|
| 1 | 0.5 mm | 10 mm |
| 2 | 0.6 mm | 13 mm |
| 3 | 0.7 mm-0.8 mm | 16 mm |
| 4 | 0.9 mm-1.1 mm | 22 mm |
| 5 | 1.2 mm-1.3 mm | 26 mm |
| 6 | 1.4 mm-1.5 mm | 30 mm |

While it is difficult to devise a precise metric for measuring the efficacy of the device of FIG. 1 one measure is to look at the rate of success of the end products, in this case the superconducting magnets made from the strand that undergoes the serpentine device and procedure of this invention, and to compare rate of success before and after incorporation of the device and procedure as in this invention. The measure of success is if the magnet which has been wound with the wire resulting from the invention can be classified as acceptable in the sense that it is capable of carrying a persistent electrical current, e.g. a decay rate of <0.1 parts per million per hour of the generated magnetic field. An undetected flaw that has been left in the wire can cause a decay rate larger than this. Each magnet in this case uses about 20 kilometers of the wire that undergoes the procedure of the invention. This difference is illustrated in Table 2, showing a clear improvement after the serpentine device and procedure was instituted, as previously undetected flaws were removed from the wire before being manufactured into a superconducting solenoid.

TABLE 2

| Sets Evaluated | Magnets made | Magnets persistent |
|----------------|--------------|---------------------|
| The last 63 sets before serpentine device | 71 | 40 (56%) |
| Since introduction of serpentine | 104 | 104 (100%) |

While the present invention has been set forth in terms of specific embodiments thereof, it will be appreciated that in view of the present disclosure, numerous variations upon the invention are now enabled to those skilled in the art, which variations yet reside within the present teachings. Accordingly the invention is to be broadly construed, and limited only by the scope and spirit of the disclosure and of the claims now appended hereto.

The invention claimed is:

1. A device for use as an adjunct in assuring that a manufactured wire is substantially free of internal flaws comprising:
    a plurality of successively adjacent wire bending stations, each station comprising on a first plane, a means for bending the wire into a second bending plane substantially parallel to the first plane, wherein the first plane and second bending plane are different for each station; and
    means for passing the wire through the successive stations;
    whereby the different bending plane at each station subjects the wire at each station to tensile bending strain at portions of the wire cross-section which are different for each station, whereby the probability is increased that a given internal flaw in the wire will be exposed to the tensile bending strain condition as the wire passes through the successive stations, increasing likelihood of breakage of the wire at the flaw or of flaw magnification to improve detection of the flaw during subsequent wire inspections.

2. A device in accordance with claim 1 where said means for bending the wire comprises planar rollers.

3. A device in accordance with claim 2 where the number of rollers at each station are two or more.

4. A device in accordance with claim 3, wherein the number of rollers are two, the wire being bent successively at a first and then at a second of the two rollers; and wherein the relative positions of the two rollers on the first plane are such that the surface of the wire being placed into tension at the first roller becomes the surface in compression at the second roller, whereby after passing through the planar set of rollers at a station, two pie slice sections around a 360° circumference of the wire have been subjected to the maximum flaw-affecting deformations.

5. A device in accordance with claim 4, where the rollers are disposed at each station on the first plane for the station, and wherein said first planes intersect on a line coincident with the wire drawing axis.

6. A device in accordance with claim 5, wherein the sets of rollers on successive stations are closely positioned along the wire drawing axis, so as to minimize the likelihood of the wire shifting angular position relative to the 360° wire circumference as the wire moves from one plane of rollers to the other.

7. A device in accordance with claim 5 wherein successive planes are positioned with an angular spacing of 120° apart, from the wire circumference reference.

8. A device in accordance with claim 3, wherein the wire path results in wire being bent over the rollers at more than 180° of the bending roll.

9. A device in accordance with claim 3 wherein the number of said bending planes are more than two.

10. A device in accordance with claim 2 where the size of the rollers is determined by the diameter of the wire and the desired bending strain to be achieved in the wire.

11. A device in accordance with claim 10 wherein the radius of the rollers is approximately equal to ten times the diameter of the wire.

12. A device in accordance with claim 1 where said subsequent wire inspection is by eddy current testing.

13. A device in accordance with claim 1 where said subsequent wire inspection is by laser micrometer diameter measurement.

* * * * *